US00PP31309P2

(12) United States Plant Patent
Hansen

(10) Patent No.: US PP31,309 P2
(45) Date of Patent: Dec. 31, 2019

(54) ***HOSTA* PLANT NAMED 'WU-LA-LA'**

(50) Latin Name: ***Hosta* hybrid (Tratt.)**
Varietal Denomination: Wu-La-La

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/350,551

(22) Filed: Nov. 30, 2018

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
See application file for complete search history.

*Primary Examiner* — Anne Marie Grunberg

(57) ABSTRACT

*Hosta* plant named 'Wu-La-La' is a new cultivar with vigorous growth rate, large plant stature; large bluish-green leaves with yellow-green margins and light lavender flowers and with matching bracts, suitable as a potted plant and for the garden.

2 Drawing Sheets

Botanical classification: *Hosta* hybrid (Tratt.).
Variety denomination: 'Wu-La-La'.

STATEMENT REGARDING PRIOR DISCLOSURES UNDER 37 CFR 1.77(b)(6)

The first public disclosure of the claimed plant, in the form of a sale, was made by Walters Gardens, Inc. on May 14, 2018. Prior to that, on Dec. 1, 2017 the claimed plant was displayed with a photograph and brief description in a website operated by Walters Gardens, Inc., who obtained the plant and all information relating thereto, from the inventor. No plants of *Hosta* 'Wu-La-La' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct *Hosta* plant, *Hosta* 'Wu-La-La' discovered as a whole plant mutation in a tissue cultured batch of *Hosta* 'Empress Wu' U.S. Plant Pat. No. 20,774 by the inventor in the Jun. 24, 2013 in the greenhouses of a wholesale perennial nursery in Zeeland, Mich., USA. The new plant has been successfully asexually propagated by division and also by sterile shoot tip tissue culture at a nursery in Zeeland, Mich. and in both systems found to be stable and reproduce identical plants that maintain the unique characteristics of the original plant.

BRIEF SUMMARY OF THE INVENTION

*Hosta* 'Wu-La-La' differs from 'Empress Wu', as well as all other *Hostas* known to the applicant. The most similar known *Hosta* cultivar is 'Wu Hoo' U.S. Plant patent application unknown. 'Empress Wu' is solid bluish-green and does not have a lighter yellow margin. 'Wu Hoo' maintains the bluish green margin longer in the season and the mature margin color is a deeper green shade of chartreuse. Other similar *Hostas* include: 'All that Jazz' (not patented), 'Eclipse' U.S. Plant Pat. No 24,625, 'Final Victory' (not patented), 'His Honor' (not patented) and 'Victory' (not patented). 'All that Jazz' has a lighter yellow to creamy yellow leaf margin and more cordate leaf blade. 'Final Victory' has shinier leaves that are lighter green in the center and brighter and lighter yellow on the margins. 'Victory' has a thinner, lighter yellowish margin on leaves that are shinier, less glaucous and have lighter green centers. 'His Honor' has shorter and broader habit, and the leaves have fewer vein pairs and more rippling. 'Eclipse' has more bluish hue in the foliage and the margin is more yellow, the leaf shape is more pointed and the leaf margin is more sinuate and the habit is shorter in foliage and flower. 'All that Jazz' and 'Victory' all have longer and more arching flower scapes.

There are over 8,300 cultivars listed on The American *Hosta* Society registry website. *Hosta* 'Wu-La-La' differs from these and all unregistered cultivars known to the inventor in the following combined traits:

1. Large foliage starting off with slight glaucous surface and becoming dull to slightly shiny on top.
2. Early variegation has chartreuse margin and the margin becomes brighter through the season.
3. Very large landscape stature.
4. Tightly compact light lavender flowers on short scapes just above foliage.
5. Each flower and bud is subtended by a large bract of a matching light lavender color.

BRIEF DESCRIPTION OF THE DRAWINGS

The photographs of the new plant demonstrate the overall appearance of the mature plant, including the unique traits, grown in a partially shaded trial garden at a wholesale perennial nursery in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
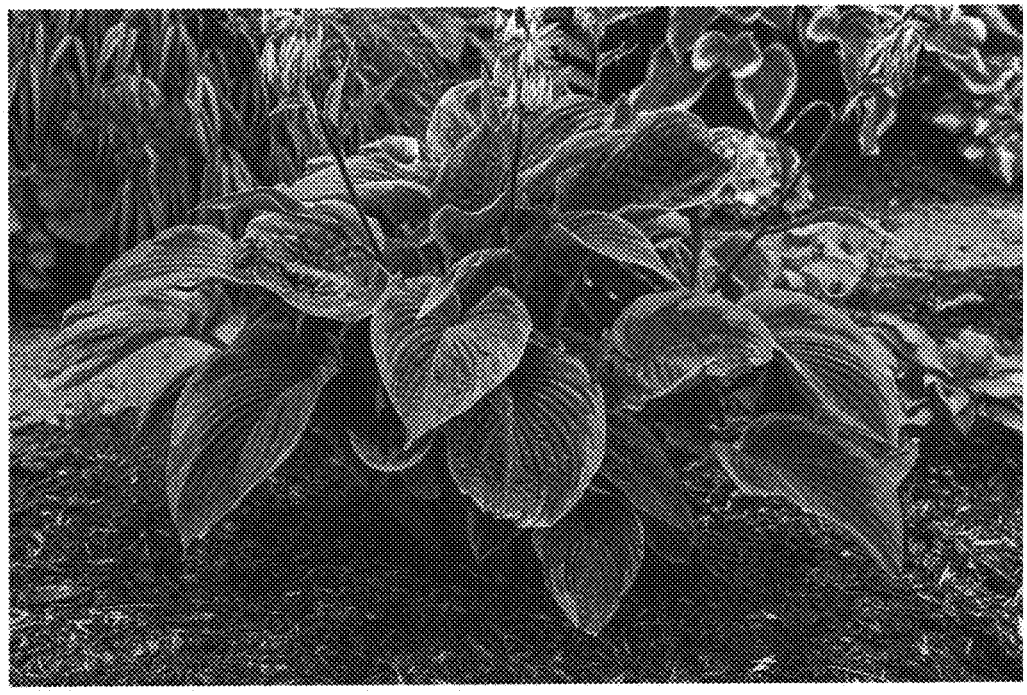
FIG. 1 shows a five-year-old plant in a landscape setting near the end of the flowering season.
Figure 2:
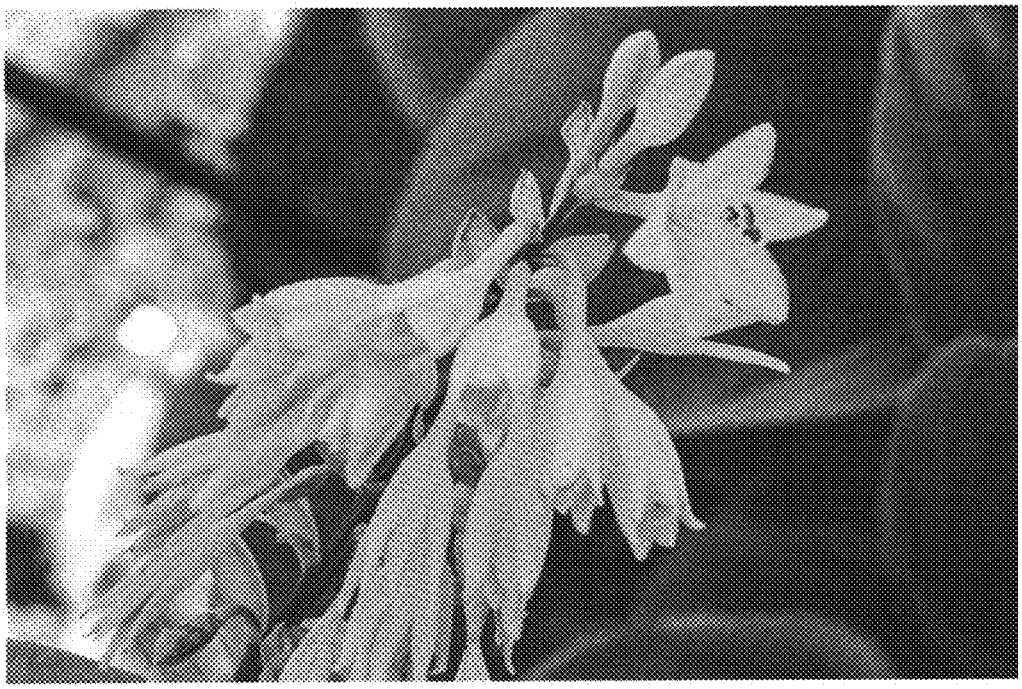
FIG. 2 shows a close-up of the flower scape.
Figure 3:
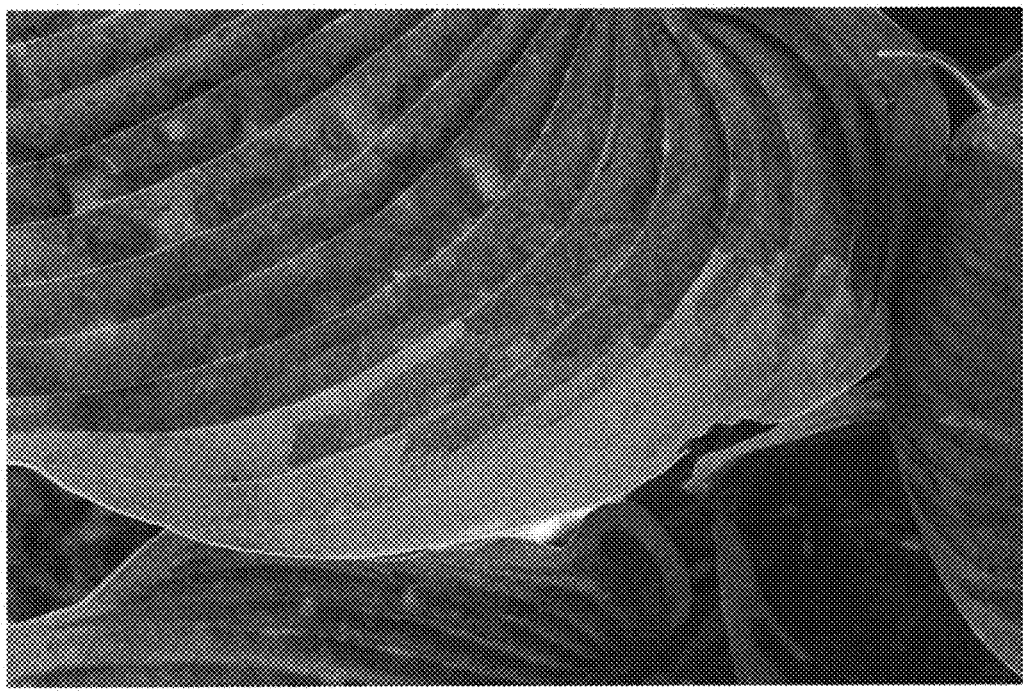
FIG. 3 shows a close-up of the top of the leaf with marginal variegation and intermediate colors.
Figure 4:
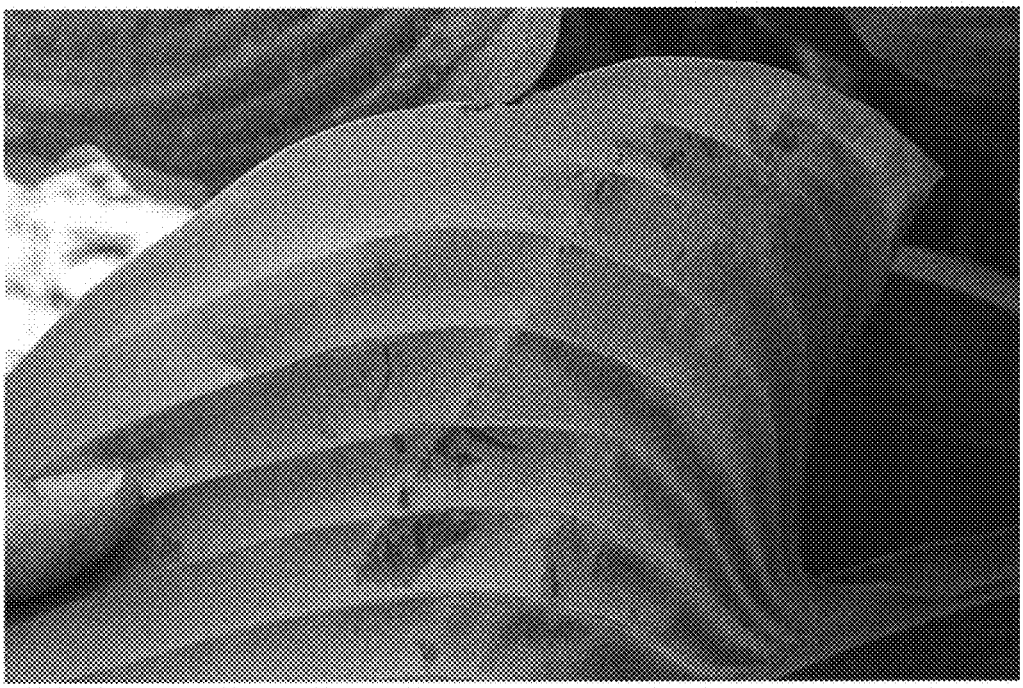
FIG. 4 shows a close-up of the back of the leaf with marginal variegation and other colors.

The following descriptions and color references are based on the 2015 edition of The Royal Horticultural Society Colour Chart except where common dictionary terms are used. The new plant, *Hosta* 'Wu-La-La', has not been observed under all possible environments. The phenotype may vary slightly with different environmental conditions, such as temperature, light, fertility, moisture and specimen maturity, but without any change in the genotype. The following observations and size descriptions are of a five-year-old plant in a partially-shaded trial garden in Zeeland, Mich.

Botanical classification: *Hosta* hybrid;

Parentage: Whole plant mutation of *Hosta* 'Empress Wu';

Propagation method: By sterile laboratory tissue culture division and garden division;

Growth rate: Rapid;

Crop time: Summer growing 8 to 9 weeks to finish in a one-liter container; Time to initiate roots from tissue culture about two weeks;

Plant description:

*Plant shape and habit.*—Hardy, herbaceous, upright as juvenile and mounded in maturity, forming perennial with basal rosette leaves, usually bilateral and radially symmetrical, spreading by short rhizomes.

*Roots.*—Normal, fleshy, lightly branching, cream-colored in normal soil, nearest RHS 164D.

*Plant size.*—Foliage height of a mature plant at flowering is about 78.0 cm tall; width of plant at the widest point is approximately 114 cm at the widest point; flower scapes to about 100.0 cm tall.

Foliage description:

*Leaf blade.*—Cordate leaf base with acute apex, mostly bilaterally symmetrical, entire margins, mostly flat blades with impressed veins; width to length ratio of about 1:1.3; largest leaves about 35.5 cm long and 26.0 cm wide; average about 32 cm long and 24 cm wide increasing with maturity age; margin width to about 20.0 mm; 17 pairs of major parallel veins; top surface begins season slightly glaucous becoming dull matte surfaced to slightly shiny, and bottom surface is glaucous and tends to stay through most of the season.

*Blade color.*—Mature adaxial center more glaucous than RHS 136A, adaxial margin nearest RHS N143D, intermediate colors between margin and center comprising between RHS 122B and RHS 122C and blend between RHS 138C and RHS 133C; mature abaxial center nearest RHS 122B with a glaucous bloom, margin nearest blend of RHS 146D and RHS 145A, intermediate zone comprising nearest RHS blend between RHS 122B and RHS 122C; spring and expanding adaxial center between RHS 138B and RHS 138C, adaxial margin blend between RHS 143C and RHS 138C; spring and expanding abaxial center nearest RHS 146C and margin nearest RHS 146D.

*Veins.*—17 Pairs of major parallel veins, deeply impressed; same color as surrounding top and bottom leaf surfaces.

*Petioles.*—To about 50 cm long, about 2.8 cm wide measured at 7 cm above soil line.

*Petiole color.*—Adaxial and abaxial petiole margin nearest RHS 145C with a slight glaucous surface; adaxial center nearest inside of petiole lighter than RHS 138C, abaxial center nearest RHS 138D.

Flower description:

*Buds.*—One day prior to opening clavate with bluntly acute apex and longer thin base; nearest RHS 91D near base and RHS 92D at middle and apex; about 3.8 cm long, and 7.0 mm wide at the broadest portion, tube to 3.0 mm diameter.

*Bud color.*—Nearest RHS 91D at base and RHS 92D at middle and apex.

*Flowers.*—28 to 36 per scape; tightly arranged with about 6 to 8 flowers per 1.0 cm centimeter of scape in some areas and spaced 1 cm apart in other areas; funnelform; about 2.8 cm wide and 4.4 cm long, (distal flowers opening smaller); remain open for a normal period, usually one to two days on or cut from plant; scapes remain effective from mid-June into mid-July in Zeeland, Mich.; no detectable fragrance.

*Tepal.*—Two identical sets of three fused at the basal two thirds; acute apex; margins entire; approximately 37.0 mm long and 8.0 mm wide (outer set) and 9.0 mm wide (inner set).

*Tepal color.*—Abaxial between RHS 76C and RHS 76D; adaxial outer set lighter than RHS 76D on margin and center nearest RHS 76C with veins nearest, adaxial inner set lighter than RHS 76D on margin, center nearest RHS 76C and veins nearest RHS 76A.

*Pedicel.*—Cylindrical; glaucous; approximately 13.0 mm long, 1.5 mm wide; attitude mostly outwardly.

*Pedicel color.*—Between RHS 138C and RHS 138B with slight violet undertones or nearest RHS 91C.

*Peduncle.*—Cylindrical; glaucous; usually one per division, erect to slightly arching, about 10.0 mm diameter at base, average 94.0 cm tall.

*Peduncle color.*—Nearest RHS N138B.

*Gynoecium.*—Single; superior; about 38.0 mm long.

*Style.*—About 38.0 mm long, 1 mm diameter, curled upward at distal 1.0 cm; color base nearest RHS 145D, nearest RHS NN155D in distal 12 mm.

*Stigma.*—1.5 mm diameter; puberulent; color nearest RHS NN155D.

*Ovary.*—Fluted longitudinally; ellipsoidal; to about 5.0 mm long and 2.8 mm across; color nearest RHS 146D.

*Androecium.*—Six.

*Filaments.*—Six; about 0.5 mm in diameter and 33.0 mm long, curving upward the last 1.0 cm; nearest RHS NN155D.

*Anthers.*—Oblong; dorsifixed; longitudinal; about 4.0 mm long and 1.5 mm wide; color back between RHS N187C and lighter than RHS N77D, front between RHS 177A and RHS 177B.

*Pollen.*—Elliptical, less than 0.1 mm long, nearest RHS 13B.

*Bracts.*—Subtending one or more flowers; lanceolate; widest at base and tapering to acute apex; truncate sessile base; protruding upward about 80 degree angle away from scape; average about 17.0 mm long and 7.0 mm wide in middle; decreasing distally and increasing proximally in both length and width.

*Bract color.*—Apical one-third nearest RHS 146B, basal two-thirds with pale tinting of nearest RHS 76B.

*Fruit.*—Tri-dehiscent capsule, about 2.8 cm long and 6.0 mm wide; variable in color at dehiscence including: RHS 164B with more green or more yellow.

*Seeds.*—Single winged drupe, about 10 mm long and 3 mm wide; about 30 per pod; black nearest RHS 202A.

*Disease resistance.*—Slug feeding on mature plants has not been noticed. Other disease or pest resistance beyond that common to Hostas has not been observed. The plant grows best with light fertilizer, plenty of moisture and adequate drainage, but is able to tolerate some flooding and drought when mature. Hardiness at least from USDA zone 3 through 9, and other disease resistance is typical of that of other *Hostas.*

I claim:

1. A new and distinct ornamental *Hosta* plant named 'Wu-La-La' as herein described and illustrated.

* * * * *